(12) United States Patent
Borck

(10) Patent No.: US 8,486,013 B2
(45) Date of Patent: Jul. 16, 2013

(54) BALLOON CATHETER HAVING COATING

(75) Inventor: Alexander Borck, Aurachtal (DE)

(73) Assignee: Biotronik AG, Buelach (CH)

( * ) Notice: Subject to any disclaimer, the term of this patent is extended or adjusted under 35 U.S.C. 154(b) by 282 days.

(21) Appl. No.: 13/006,754

(22) Filed: Jan. 14, 2011

(65) Prior Publication Data

US 2011/0230831 A1    Sep. 22, 2011

Related U.S. Application Data

(60) Provisional application No. 61/315,052, filed on Mar. 18, 2010.

(51) Int. Cl.
*A61M 31/00* (2006.01)

(52) U.S. Cl.
USPC .................................... 604/103.02

(58) Field of Classification Search
USPC .......................................... 604/96.01, 103.02
See application file for complete search history.

(56) References Cited

U.S. PATENT DOCUMENTS

| | | | |
|---|---|---|---|
| 4,784,659 A * | 11/1988 | Fleckenstein et al. | 623/1.45 |
| 5,447,966 A * | 9/1995 | Hermes et al. | 523/113 |
| 6,909,220 B2 * | 6/2005 | Chen | 310/309 |
| 2001/0036472 A1 * | 11/2001 | Wong et al. | 424/456 |
| 2004/0062804 A1 * | 4/2004 | Lee et al. | 424/471 |
| 2005/0019366 A1 * | 1/2005 | Zeldis | 424/423 |
| 2005/0187607 A1 * | 8/2005 | Akhtar et al. | 623/1.15 |
| 2005/0229264 A1 * | 10/2005 | Chang et al. | 800/8 |
| 2008/0058923 A1 * | 3/2008 | Bertsch et al. | 623/1.46 |
| 2010/0008989 A1 * | 1/2010 | Attar et al. | 424/484 |
| 2011/0106243 A1 * | 5/2011 | Van Dongen et al. | 623/1.46 |
| 2011/0230831 A1 * | 9/2011 | Borck | 604/103.02 |
| 2011/0274820 A1 * | 11/2011 | Axelsson et al. | 427/2.22 |
| 2011/0287093 A1 * | 11/2011 | Schoenhard | 424/456 |

* cited by examiner

*Primary Examiner* — Nicholas Lucchesi
*Assistant Examiner* — Diva K Chander
(74) *Attorney, Agent, or Firm* — Greer, Burns & Crain, Ltd.

(57) ABSTRACT

An embodiment of the present invention relates to a balloon catheter, which has a drug-releasing coating and/or cavity filling on at least parts of the outwardly facing surface of the dilatable balloon, characterized in that the coating comprises a drug and a gelatin mixture, the gelatin components of the gelatin mixture comprising 10-90 wt. % high-bloom gelatin having a gel strength of $\geq 250$ bloom and 90-10 wt. % medium-bloom gelatin having a gel strength of $\geq 50$ to $<250$ bloom, the specifications in wt. % relating to the total weight of the gelatin components of the gelatin mixture.

20 Claims, No Drawings

BALLOON CATHETER HAVING COATING

CROSS REFERENCE

The present application claims priority on U.S. Provisional Application No. 61/315,052 filed on Mar. 18, 2010; which application is incorporated herein by reference.

TECHNICAL FIELD

Some invention embodiments concern a balloon catheter, a method for its production and a coating for the balloon catheter.

BACKGROUND

Angioplasty, also referred to as percutaneous transluminal angioplasty (PTA) or percutaneous transluminal coronary angioplasty (PTCA), is a method for the widening or reopening of constricted or closed blood vessels (typically arteries, more rarely also veins). A common method of angioplasty is balloon dilation.

Balloon dilation in the context of angioplasty is understood in interventional radiology, cardiology, and vascular medicine as a method for expanding pathologically constricted blood vessels using a balloon catheter, a vascular catheter having balloon attached thereto, which only unfolds slowly under high pressure (often 6-20 bar) at the constricted location. The narrow points, which arise, inter alia, due to atherosclerotic changes (vascular calcification), are thus stretched so that they no longer obstruct the blood flow or obstruct it less.

The balloon catheter is almost always placed from the groin via a guide wire and guide catheter in the stenosis (narrow point) and inflated using pressure. The narrow point is typically remedied in this way and an operation is avoided.

Modern methods in the field of plastic processing allow the design and refinement of such balloons to adapt the quality individually to the requirements of the patients. The flexibility of the balloons and their pressure resistance are important for this purpose.

The drug-releasing balloon catheter (also known as a drug-eluting balloon or drug-coated balloon) is a refinement of the typical balloon catheter.

The balloon surface is at least partially coated with a drug or medication, which is applied at the point of the vascular constriction by the dilation of the balloon, in order to pharmacologically support and stabilize the vascular expansion. In contrast to stent therapy, a mechanically acting foreign body does not remain in the body after the intervention.

A cytostatic agent, for example, paclitaxel because of its rapid penetration into the vascular wall, can be used as the drug for this purpose. In addition, an additive is frequently added to the medication, which encourages the absorption of the medication in the vascular wall.

Various methods are known for applying drugs or medications to a balloon catheter:
1) embedding the drug in a microporous surface of the balloon;
2) coating the balloon with drug-containing polymer layers (base coating, drug depot).

In the typical method, the majority of the drug is applied below the folds of the non-dilated balloon. An uneven distribution of the drug over the dilated balloon surface and later also over the surface of the dilated vessel thus results.

The drug is frequently applied to the balloon by immersion or spraying. The externally remaining component of the drug can flake off in an uncontrolled manner upon the later dilation, so that the release of the introduced drug also cannot be exactly controlled.

During the insertion and positioning of the catheter at the action location, the catheter is also subject to greatly varying mechanical strains, which may result in the loss of the coating. These include, for example, the removal of the protector, touching of the balloon by the operator, buckling of the balloon, the insertion of the catheter into the so-called "introducer", the friction in the guide catheter, friction on the vascular wall or other materials such as blood in the vessel, and, in particular with calcified lesions, a high level of mechanical influence.

The loss of pharmacologically active substance already on the way to the target location makes it necessary to charge the balloon catheter with a significantly higher quantity of drug than would actually be necessary for the desired effect.

SUMMARY

One object of the present invention is to reduce or avoid one or more disadvantages of the prior art.

Some embodiments of the present invention achieve this and other objects by providing a balloon catheter, which has a drug-releasing coating and/or cavity filling on at least parts of the outwardly facing surface of the dilatable balloon, characterized in that the coating comprises a drug and a gelatin mixture, the gelatin components of the gelatin mixture comprising 10-90 wt. % high-bloom gelatin having a gel strength of $\geqq 250$ bloom and 90-10 wt. % medium-bloom gelatin having a gel strength of $\geqq 50$ to <250 bloom, the specifications in wt. % relating to the total weight of the gelatin components of the gelatin mixture. Many other concentration and bloom ranges are possible within the scope of the invention.

DETAILED DESCRIPTION

Before discussing further aspects of the invention in detail, it will be appreciated that the present invention includes apparatuses, methods for making the apparatuses, and methods for using the apparatuses. In describing one embodiment, description of another may be had. When describing an apparatus of the invention, for example, description may also be had of a method for making the apparatus.

Through the solution according to at least some invention embodiments, the loss of drug before the balloon catheter reaches the lesion is prevented. The drug is embedded in a gelatin matrix. It has been discovered that a gelatin gel having included drug, with an example being paclitaxel, adheres outstandingly to balloon materials. Other drugs may be used as desired and as are suitable for different applications, with an example being cytostatic agents and mitotic inhibitors other than paclitaxel and other drugs. Gelatin is particularly suitable in this case, because the dissolving process of the gelatin begins at body temperature. The drug-bearing matrix is thus already subjected to the body temperature after the implantation and begins to dissolve. As soon as the instrument reaches the target location and the balloon is dilated, the matrix solution finds its peak and the medication can be released immediately and over a short period of time, which may be for example less than 5 minutes, less than 10 minutes, less than 30 minutes, or other periods. Even if the matrix is not completely dissolved, the drug release is hardly obstructed by the hydrogel nature of the matrix, so that even if the matrix is still partially intact, the drug is released at the implantation location by the dilation.

The sliding properties of the instrument provided with a gelatin layer are significantly improved due to the low coefficient of friction of the gelatin layer and other invention features. Irritation of healthy tissue and stenosis after the guide catheter is fed through are avoided. The coating of medication-coated balloon catheters is thus protected from loss of the coating during the handling (exo-coating). This results in a more homogeneous and more tightly controlled distribution of the drug on the lesion and less systemic strain of the patient. The quantity of drugs on the balloon catheter can thus be reduced overall, without impairing the clinical effect.

Through the coating with gelatin, the drug is fixed on the balloon and protected from mechanical strains and abrasion during handling, insertion and travel in the body to the desired location of deployment. After the dilation, the swollen gelatin becomes water-soluble due to the ambient temperature. The drug is released at the target location. The balloon catheter displays significantly enhanced sliding properties through the gelatin coating. This is advantageous in particular upon the treatment of in-stent restenosis (ISR), because complicated stenoses may also be reached and treated in this way.

Fundamentally, any known balloon catheter system can be used for the balloon catheter according to the invention. One useful embodiment of the invention relates in particular to a balloon catheter having an internal shaft, on which a dilatable balloon is fastened on the distal end, which at least partially presses against an external surface of the internal shaft in a non-expanded, deflated state. The invention particularly relates to those catheters which carry a drug on the outer side of the dilatable balloon, which, after the insertion of the catheter into a vessel and subsequent dilation of the balloon at the desired vascular section, presses against a vascular wall and is at least partially discharged there.

Balloon catheters of the provided type typically also have, in addition to an internal shaft and the dilatable balloon, an external shaft, which extends at least up to a proximal end of the balloon and is connected fluid-tight thereto. A fluid line, which reaches in the longitudinal direction of the catheter from its proximal end up into the interior of the balloon, is typically provided between the internal and external shafts of the catheter, which results, for example, because the external shaft has an internal diameter which is greater than an external diameter of the internal shaft.

A cavity which is enclosed by the internal shaft and extends in the longitudinal direction of the internal shaft is provided as a lumen in the interior of the internal shaft. This lumen is used, for example, to receive a mandrin or a guide wire. Catheter and guide wire are then implemented, for example, so that the guide wire can exit at the distal tip of the catheter and is to be controlled from the proximal end. The guide wire is deflected with the aid of control means, for example, so that it is also easy to insert into branching blood vessels. The balloon catheter can then be pushed along following the guide wire.

Independently of the type of the guide wire, in particular with respect to the design of the guide means, balloon catheters have the dilatable balloon already described on their distal end. During the insertion of the balloon catheter, the balloon is compressed and presses tightly against the internal shaft of the catheter. The balloon can be expanded by inflating it using a fluid. This expansion of the fluid occurs as soon as the balloon has been guided up to the intended position. A surface of the balloon is pressed against a vascular wall by the expansion of the balloon. This occurs, for example, for the purpose of widening vascular constrictions (stenoses) using the balloon catheter. A drug applied to the external surface of the balloon can be discharged to the vascular wall.

The balloon catheter according to at least some embodiments of the invention has a drug-releasing coating and/or cavity filling on at least parts of the external surface of the dilatable balloon. The coating can also cover the entire external surface of the balloon. A coating in the meaning of the invention is an at least sectional application of the components of the coating on the external surface of the dilatable balloon of the catheter. The surface of the balloon which can typically be contacted or is brought into contact with the vascular wall during clinical use is designated as the external surface. In many (but not all) embodiments, the entire external surface of the balloon is covered by the coating. A layer thickness may be selected as desired and depending on application. Examples include thicknesses in the range of 1 nm to 100 µm, and 300 nm to 50 µm. Other thicknesses, including less than 1 nm and greater than 50 µm, may also be useful in some applications. The coating can be applied directly to the balloon surface, or otherwise. The processing can be performed according to standard methods for coating. Single-layer, or also multilayer systems (for example, so-called base coat layers, drug coat layers, or drug-comprising top coat layers) may be prepared. The coating can be applied directly to the balloon body or further layers may be provided in between.

The balloon catheter can alternatively or additionally have a cavity filling. The cavity is typically located on the external surface of the dilatable balloon, although other locations may also be utilized.

Methods for coating balloon catheters and for applying cavity fillings to balloon catheters are known to those skilled in the art, and for sake of brevity need not be discussed in detail herein.

The coating of the balloon catheter according to invention embodiments comprises a drug which can be released therefrom, and a gelatin mixture. In some embodiments, the gelatin components of the gelatin mixture comprising 10-90 wt. % high-bloom gelatin having a gel strength of $\geq 250$ bloom and 90-10 wt. % medium-bloom gelatin having a gel strength of $\geq 50$ to <250 bloom, the specifications in wt. % relating to the total weight of the gelatin components of the gelatin mixture. In many embodiments, the wt. % of high-bloom gelatin and the wt. % of medium-bloom gelatin add up to 100% of the total weight of the gelatin components of the gelatin mixture. The high-bloom gelatin in some embodiments has a gel strength of $\geq 250$ to 400 bloom, and in some others from $\geq 250$ up to 300 bloom inclusive.

As will be appreciated by those knowledgeable in the art, the "bloom" as a unit describes the gel strength of gelatin. The parameter specifies the mass in grams which is required to make a plunger of 0.5 inches diameter deform the surface of 112 g of a 6.67% (w/w) gelatin 4 mm deep. The bloom value is higher the higher the gel strength of the gelatin. The bloom determination is performed in standardized form at +10° C., the gelatin blank to be tested previously having been cured for 17 hours at +10° C. A gelatometer according to Bloom can be used for the bloom determination. The method for bloom determination is described and established, for example, in BS 757: "*Methods for Sampling and testing gelatin*", British Standard Institution, 1975.

In some invention embodiments, the gelatin components of the gelatin mixture in the coating and/or the cavity filling of the balloon catheter may be 25 to 75 wt. % high-bloom gelatin and 75 to 25 wt. % medium-bloom gelatin, or 40 to 60 wt. % high-bloom gelatin and 60 to 40 wt. % medium-bloom gelatin, or 50 wt. % high-bloom gelatin and 50 wt. % medium-bloom gelatin, for example, the specifications in wt. % each relating to the total weight of the gelatin components of the gelatin mixture. Other compositions and components may also be provided.

Gelatin is a mixture of polypeptides, having molecular masses of approximately 13,500 to 500,000 g/mol depending on how it is obtained (determined by SDS gel electrophoresis or gel chromatography), which is obtained by varying levels of hydrolysis of collagens. The amino acid composition substantially corresponds to that of collagen, from which it was obtained, and comprises all essential amino acids with the exception of tryptophan and methionin; the primary amino acid is hydroxyprolin. Gelatin often contains 84 to 90 wt. % protein and 2 to 4 wt. % mineral materials; the remainder comprises water. Gelatin is odorless and practically colorless, insoluble in ethanol, ethers, and ketones, but soluble in ethylene glycol, glycerol, formamide, and acetic acid. One differentiates between two different modes of production: the acid method for gelatin of type A and the alkaline method for gelatin of type B. The raw material for type A gelatin (predominantly pork rind) is subjected to a three-day digestion process. During the production of type B gelatin, bovine connective tissue (middle layer between the leather and the subcutaneous tissue) and/or bones are treated for 10-20 days using alkali. The strength of the gelatinous mass is determined using a gelatometer (texture analyzer) and specified as the bloom number. The isoelectric point of gelatin is at pH 7.5 to 9.3 (type A) or 4.7 to 5.2 (type B).

Gelatin can be chemically modified and widely varied in its properties by reaction of the amino groups above all with monofunctional or polyfunctional reagents, such as acylation agents, aldehydes, epoxides, halogen compounds, cyanamide, or activated unsaturated compounds. The gelatin derivatives thus obtained are included by the term gelatin in the present case.

The gelatin used according to the invention is highly biocompatible and biodegradable. The processing can be performed according to standard methods.

For processing, the gelatin is liquefied by heating, for example, using microwaves, and the drugs are suspended or dissolved. The addition is to be performed before the gelling, i.e., formation of a gel, in particular a hydrogel.

The setting of the gelatin for the coating/filling of cavities can be performed in buffered solutions. These solutions may be processed particularly simply. The pH value of the solutions is preferably in the range from pH 5 to pH 8, in order to avoid hydrolysis of the gelatin during the processing, which would result in a lower gel strength. Other pH's may be used, however.

The coating and/or cavity filling of the external surface of the dilatable balloon of a balloon catheter can be performed according to known methods, for example, application by spraying, dripping, immersion, condensation, atomization, vaporization, and/or electroplating. Other methods may be used.

Gelatin is fundamentally suitable as a carrier material for receiving drugs. The coating of the balloon catheter according to the invention is not fundamentally restricted to the use of a specific drug. Drugs having a cytostatic effect can be used, in particular, paclitaxel is used in some (but not all) embodiments.

In many embodiments, the coating and/or cavity filling can be distinguished in particular in that the uppermost layer contains the gelatin mixture. The "uppermost layer" is understood as the layer of the coating and/or cavity filling which is closest to the vascular wall or is preferably even brought into direct contact with the vascular wall after completed inflation of the coated balloon.

The drug to be released can be dissolved or suspended or otherwise placed in the layer containing the gelatin mixture or the drug-carrying layer is covered by the layer which contains the gelatin mixture. It is also possible that the drug is both dissolved or suspended in the layer containing the gelatin mixture and is also contained in a layer lying underneath.

In particular, the layer containing the gelatin mixture can be provided as a gel or hydrogel, in which the drug can be embedded, dissolved, or suspended.

The gel layer can contain 1 to 20 wt. % gelatin mixture, 5 to 10 wt. %, or other amounts as may be useful depending on application and other parameters. The specifications in wt. % relating to the total weight of the gel layer.

The drug can also be a component of the gel layer containing the gelatin mixture. The drug can make up 1 to 30 wt. % of the gel layer, 10 to 20 wt. %, or other amounts as may be useful depending on application and other parameters. The specifications in wt. % relating to the total weight of the gel layer.

The present invention also relates to a method for producing a balloon catheter according to the invention, the characteristic method step comprising the application of the drug-releasing coating and/or cavity filling. This can be performed, for example, in that the external surface of the dilatable area of the balloon catheter is at least partially coated using a coating which contains the gelatin mixture and the drug, the drug being able to be dissolved or suspended in the solution. The solvent of the solution can be water or a buffered aqueous medium. In particular, the solution can contain 5 to 10 wt. % gelatin mixture and 1 to 30 wt. % drug, the drug being able to be provided in dissolved form or suspended in the solution and the specifications in wt. % relating to the total weight of the solution. Other concentration ranges are possible.

The balloon catheter can be coated using the above-mentioned solution, for example, by spraying, dripping, immersion, condensation, atomization, vaporization, and/or electroplating.

The method described above for coating drug-releasing balloon catheters fixes the drug on the balloon using gelatin as the drug-carrying matrix. Through this fixing, the majority of the medication reaches the intended location. The chemical nature of the gelatin allows the drug to be quantitatively released at the intended location. The gelatin used is soluble at body temperature. These and other features of invention embodiments achieve important advantages over the prior art. As an example, loss of drug from the catheter as it travels to the desired end location is minimized as compared to the prior art, with the result that more accurate drug loadings and delivery are achieved.

The present invention also relates to a use of a gelatin mixture for coating a balloon catheter. In one example embodiment, the gelatin components of the gelatin mixture comprising 10-90 wt. % high-bloom gelatin having a gel strength of $\geq 250$ bloom and 90-10 wt. % medium-bloom gelatin having a gel strength of $\geq 50$ to $<250$ bloom, the specifications in wt. % relating to the total weight of the gelatin components of the gelatin mixture. In a preferred use, the wt. % of the high-bloom gelatin and the medium-bloom gelatin add up to 100 wt. % of the gelatin components of the gelatin mixture.

The invention is explained in greater detail hereafter on the basis of exemplary embodiments. These embodiments are examples only, and do not limit the scope of the invention.

EXEMPLARY EMBODIMENT 1

The paclitaxel (Ptx) is added in a concentration of 1-30%, preferably 10-20%, to a 5-25% gelatin solution, preferably 10%. The drug is suspended in the solution because of the low solubility of the Ptx in aqueous media. The solution is applied to the balloon by an immersion or spraying process and gelled at 5-10° C.

After drying, the implant is storable.

As a very lipophilic substance, Ptx can alternately be dissolved in the aqueous phase via the addition of surfactants such as Brji 35 or Triton X100.

EXEMPLARY EMBODIMENT 2

A balloon catheter is coated with Ptx and subsequently immersed in a 10% gelatin solution. Because of the lipophilic properties of the Ptx, drug is not lost. The thin top coat is gelled at 5-10° C.

After drying, the implant is storable.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A balloon catheter with improved sliding properties and comprising a dilatable balloon, which has a one or more of a drug-releasing coating and cavity filling on at least parts of the outwardly facing surface of the dilatable balloon, characterized in that the coating comprises a drug and a gelatin mixture, the gelatin components of the gelatin mixture comprising 10-90 wt. % high-bloom gelatin having a gel strength of $\geq$250 bloom and 90-10 wt. % medium-bloom gelatin having a gel strength of $\geq$50 to <250 bloom, the specifications in wt. % relating to the total weight of the gelatin components of the gelatin mixture; wherein the drug is fixed on the dilatable balloon and protected from mechanical strains and abrasion through the coating.

2. A balloon catheter according to claim 1, characterized in that the high-bloom gelatin has a gel strength of $\geq$250 to 400 bloom.

3. A balloon catheter according to claim 1, characterized in that the gelatin components of the gelatin mixture comprise 25 to 75 wt. % high-bloom gelatin and 75 to 25 wt. % medium-bloom gelatin.

4. A balloon catheter according to claim 1, characterized in that the drug is paclitaxel.

5. A balloon catheter according to claim 1, characterized in that the uppermost layer of the one or more drug-releasing coating and cavity filling contains the gelatin mixture.

6. A balloon catheter according to claim 5, characterized in that the drug is one of covered by the layer containing the gelatin mixture or is dissolved or suspended therein.

7. A balloon catheter according to claim 1, characterized in that the one or more of the layer of the coating and the cavity filling containing the gelatin mixture is provided as a gel.

8. A balloon catheter according to claim 7, characterized in that the gelatin mixture makes up 1 to 20 wt. % of the gel layer, the specifications in wt. % relating to the total weight of the gel layer.

9. A balloon catheter according to claim 7, characterized in that the drug makes up 1 to 30 wt. % of the gel layer the specifications in wt. % relating to the total weight of the gel layer.

10. A balloon catheter according to claim 1, made according to a method characterized in that the external surface of the dilatable area of the balloon catheter is at least partially coated using a solution which contains the gelatin mixture and the drug, the drug one of dissolved or suspended in the solution.

11. A balloon catheter according to claim 10, characterized in that the solution contains 5 to 10 wt. % gelatin mixture and 1 to 30 wt. % drug, the drug being one of dissolved or suspended in the solution.

12. Use of a gelatin mixture for coating a balloon catheter, characterized in that the gelatin components of the gelatin mixture comprise 10-90 wt. % high-bloom gelatin having a gel strength of $\geq$250 bloom and 90-10 wt. % medium-bloom gelatin having a gel strength of $\geq$50 to <250 bloom, the specifications in wt. % relating to the total weight of the gelatin components of the gelatin mixture.

13. A balloon catheter according to claim 1, characterized in that the high-bloom gelatin has a gel strength of $\geq$250 to 300 bloom.

14. A balloon catheter according to claim 1, characterized in that the gelatin components of the gelatin mixture comprise 40 to 60 wt. % high-bloom gelatin and 60 to 40 wt. % medium-bloom gelatin.

15. A balloon catheter according to claim 1, characterized in that the gelatin components of the gelatin mixture comprise about 50 wt % high-bloom gelatin and 50 wt. % medium-bloom gelatin.

16. A balloon catheter according to claim 7, characterized in that the gelatin mixture makes up 5 to 10 wt. % of the gel layer.

17. A balloon catheter according to claim 7, characterized in that the drug makes up 10 to 20 wt. % of the gel layer.

18. A balloon catheter comprising:
a shaft having ends;
a dilatable balloon connected to one of the shaft ends and having an outwardly facing surface;
one or more of a drug-releasing coating and cavity filling on at least parts of the outwardly facing surface, the one or more coating and filling each comprising a cytostatic drug and a gelatin mixture, the gelatin components of the gelatin mixture comprising:
25-75 wt. % high-bloom gelatin (wt. % relating to the total weight of the gelatin components of the gelatin mixture) having a gel strength of between 250 and 400 bloom; and,
75-25 wt. % medium-bloom gelatin having a gel strength of between 50 and 250 bloom.

19. A balloon catheter as defined by claim 18, wherein:
the uppermost layer of the one or more drug releasing coating and cavity filling contains the gelatin mixture and the cytostatic drug is covered by the uppermost layer;
the gelatin mixture is provided as a gel; and,
the gelatin components of the gel comprise 40-60 wt. % the high-bloom gelatin and 60-40 wt % the medium-bloom gelatin.

20. A balloon catheter as defined by claim 18, wherein:
the cytostatic drug is paclitaxel;
the one or more of the layer of the coating and the cavity filling containing the gelatin mixture is provided as a gel, the paclitaxel is a component of the gel layer, and the gelatin comprises 1 to 20 wt % of the gel layer and the paclitaxel comprises 10 to 20 wt % of the gel layer.

* * * * *